US011192874B2

(12) United States Patent
Ortolano et al.

(10) Patent No.: US 11,192,874 B2
(45) Date of Patent: Dec. 7, 2021

(54) USE OF PHARMACOLOGICAL CHAPERONES FOR THE TREATMENT OF LYSOSOMAL STORAGE DISEASES

(71) Applicants: FUNDACION BIOMEDICA GALICIA SUR, Vigo (ES); UNIVERSIDAD DE VIGO, Vigo (ES)

(72) Inventors: Saida Ortolano, Vigo (ES); Pedro Besada Pereira, Vigo (ES); Carmen Teran Moldes, Vigo (ES)

(73) Assignees: FUNDACION BIOMEDICA GALICIA SUR, Vigo (ES); UNIVERSIDAD DE VIGO, Vigo (ES)

( * ) Notice: Subject to any disclaimer, the term of this patent is extended or adjusted under 35 U.S.C. 154(b) by 0 days.

(21) Appl. No.: 16/771,512

(22) PCT Filed: Dec. 10, 2018

(86) PCT No.: PCT/ES2018/070794
§ 371 (c)(1),
(2) Date: Jun. 10, 2020

(87) PCT Pub. No.: WO2019/115854
PCT Pub. Date: Jun. 20, 2019

(65) Prior Publication Data
US 2021/0179575 A1 Jun. 17, 2021

(30) Foreign Application Priority Data
Dec. 11, 2017 (ES) .................. P201731396

(51) Int. Cl.
C07D 309/12 (2006.01)
A61P 3/00 (2006.01)
(52) U.S. Cl.
CPC .............. *C07D 309/12* (2013.01); *A61P 3/00* (2018.01)
(58) Field of Classification Search
None
See application file for complete search history.

(56) References Cited
U.S. PATENT DOCUMENTS
4,225,590 A 9/1980 Waites et al.

FOREIGN PATENT DOCUMENTS
EP 2143420 B1 6/2014
WO 9811206 A2 3/1998
WO 2014014938 A1 1/2014

OTHER PUBLICATIONS

CAS 18908-44-6 (entered into STN 1984) (Year: 1984).*
Frustaci etal (NEJM 345:25-32, 2001) (Year: 2001).*
Williams etal (Foye's Principles of Medicinal Chemistry, 5th Ed., pp. 59-63, 2002) (Year: 2002).*
Frustaci et al., "Improvement in cardiac function in the cardiac variant, of Fabry's disease with galactose-infusion therapy",The New England Journal of Medicine, 2001, vol. 345, No. 1, pp. 25-32.
Shin et al., "Prediction of response of mutated alpha-galactosidase A to a pharmacological chaperone", Pharmacogenetics and Genomics, 2008, vol. 18, No. 9, pp. 1-16.
Kovacs et al., "Unprotected sugar phosphinimines: A facile route to cyclic carbamates of amino sugars", Carbohydrate Research, 1985, vol. 141, No. 1, pp. 57-65.
Burland et al., "Synthesis and glycosidase inhibitory profiles of functionalised morpholines and oxazepanes", Bioorganic & Medicinal Chemistry, 2011, vol. 19, No. 18, pp. 5679-5692.
Okeley et al., "Metabolic Engineering of Monoclonal Antibody Carbohydrates for Antibody-Drug Conjugation", Bioconjugate Chemistry, 2013, vol. 24, No. 10, pp. 1650-1655.
Lin et al., "Chemoenzymatic Synthesis of GDP-L-Fucose Derivatives as Potent and Selective [alpha]-1,3-Fucosyitransferase Inhibitors",Advanced Synthesis & Catalysis, 2012,vol. 354, No. 9, pp. 1750-1758.
International Search Report and Written Opinion for Corresponding International Application No. PCT/ES2018/070794 (14 Pages) (dated May 15, 2019).
International Preliminary Report of Patentability for Corresponding International Application No. PCT/ES2018/070794 (26 Pages) (dated Mar. 11, 2020).

* cited by examiner

*Primary Examiner* — Craig D Ricci
(74) *Attorney, Agent, or Firm* — Lucas & Mercanti, LLP

(57) ABSTRACT

The present invention relates to the use of galactose analogues of formula (I) with the capacity to stabilize the structure of the #-GalA enzyme, for the treatment of lysosomal storage diseases and, in a preferred embodiment, for the treatment of Fabry disease. In addition, the present invention relates to pharmacological compositions having an effective amount of at least one of the galactose analogues described in the present document for the treatment of lysosomal storage diseases and, in a preferred embodiment, for the treatment of Fabry disease.

3 Claims, 3 Drawing Sheets

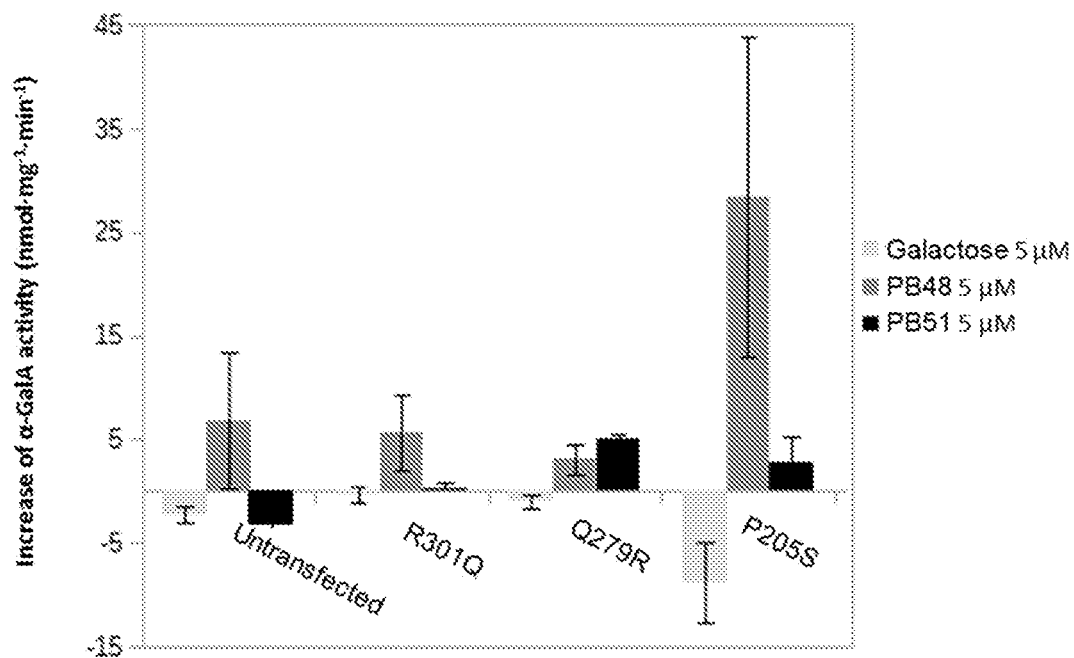
Figure 1.A
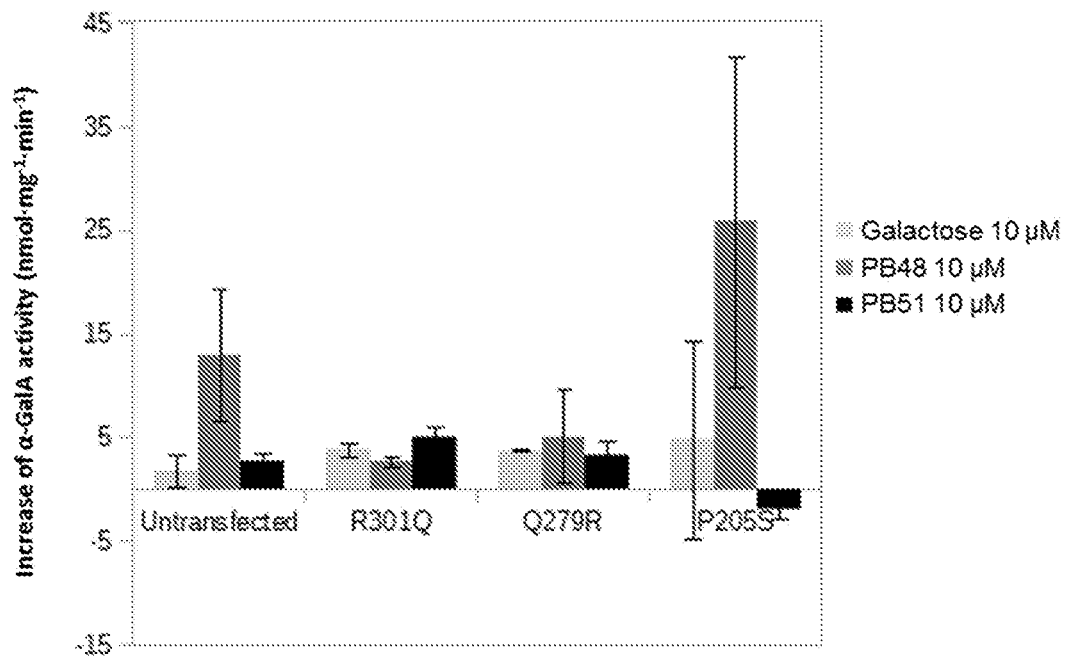
Figure 1.B

USE OF PHARMACOLOGICAL CHAPERONES FOR THE TREATMENT OF LYSOSOMAL STORAGE DISEASES

CROSS REFERENCE TO RELATED APPLICATION

This Application is a 371 of PCT/ES2018/070794 filed on Dec. 10, 2018, which claims the benefit of Spanish Patent Application No. P201731396, filed Dec. 11, 2017, which is incorporated herein by reference.

FIELD OF THE INVENTION

The present invention belongs to the pharmaceutical and chemistry field. More particularly, the present document relates to the use of new pharmacological chaperones for the treatment of lysosomal storage diseases.

BACKGROUND OF THE INVENTION

Metabolic diseases, referred to as storage or lysosomal storage diseases, are known in the state of the art. The main cause of these diseases, is that an enzyme responsible for metabolizing a particular substrate, present some mutation in the gene that encodes it, reducing or even suppressing its metabolic activity, causing the accumulation of the substrate.

A well-known example of this kind of diseases is Fabry Disease (FD) which is a hereditary disease linked to X chromosome and caused by an impairment of α-galactosidase A (α-GalA), a hydrolytic enzyme expressed in the lysosomes and encoded by the GLA gene (position Xq22). This deficit determines the misfolding of the enzyme, causing the accumulation of unmetabolized substrates such as globotriaosylceramide (Gb3) and other structurally related glycosphingolipids (eg. LysoGb3). Deposits of unmetabolized substrates in the vascular endothelium as well as in other cells from different organs, cause progressive systemic manifestations (eg. Renal failure, cardiomyopathy and juvenile stroke) that increase the risk of early death. Deposits also affect the patients' quality of life by causing other clinical manifestations, such as chronic neuropathic pain and gastrointestinal diseases, among others.

Fabry Disease is considered a rare disease, since it has an estimated incidence of 1:7000 live births, although the experts consider that the number of potential affected people could be higher, as supported by the data obtained in the newborn screening studies that are being performed routinely in different countries.

Current treatment for FD is based on Enzyme Replacement Therapy (ERT), consisting in the intravenous administration of recombinant human α-GalA (agalsidase alpha and agalsidase beta). ERT facilitates removal of endothelial vascular deposits and slows down the progression of the disease, while improving some aspects of the patients' quality of life (i.e. decrease of pain crises).

In this therapeutic field, the patent applications WO9811206A2 and US200471686 (A1) exist, which describe the treatment of a disease characterized by α-GalA deficiency, and particularly Fabry disease, based on the administration of purified human α-GalA which is obtained from the use of genetically modified cell lines overexpressing and secreting recombinant human α-GalA.

However, the enzyme replacement therapies currently authorized have several limitations such as:

1. They are escacely compliant for the patients, since they are administered as intravenous infusion of 40-60 min every 2 weeks (as the half-life of the available drugs in the body is low).
2. The distribution throughout the body of the patient is heterogeneous.
3. They do not cross the blood-brain barrier (BBB), being inactive against the symptoms in the central nervous system.
4. There is a risk of inactivation of the drug due to the response of the adaptative immune system.
5. These biological drugs have, also, a high production cost due to the high risk of contamination during the process, which can lead to significant economic losses.

There are also other therapeutic alternatives that are in development, such as, gene therapy, in vivo or ex vivo. In addition to these alternatives therapies therapeutic molecules known in the state of the art with the definition of pharmacological chaperones (PCs) also exist, being one of the aforementioned pharmacological chaperones already approved by the European Medicine Agency (EMA).

In this therapeutic field, the research group of Dr. Fan synthesized the first PC for FD therapy, named 1-deoxygalactonojirimycin (DGJ), which is a competitive inhibitor of α-GalA. This iminosugar is the active component of Migalastat hydrochloride (Galafold®, Amicus Therapeutics), a drug that showed good results in Phase III clinical trials (NCT01458119, NCT00925301, https://clinicaltrials.gov) and obtained EMA approval in July 2016 for its commercialization. This study is related to the patent EP2143420 B1, which describes the method to increase the lysosomal α-GalA (±) activity in mammalian cells and the treatment of Fabry disease by the administration of DGJ and related compounds. The study is also related to the patent application EP2874648A1 which describes the administration of pharmacological compositions comprising this drug. It has been demonstrated that DGJ is effective at low concentrations to restore α-GalA activity in those mutations responsible for the disease that cause a misfolding of the α-GalA enzyme, preventing its transport from the endoplasmic reticulum, causing the accumulation of the mutated enzyme. This accumulation of mutated α-GalA causes aggregation and subsequent degradation of the enzyme, which is prevented to reach the lysosomes, place where it should perform its metabolic activity. Therefore, the action mechanism of this drug focuses on binding to the mutated enzyme to prevent aggregation at the endoplasmatic reticulum and subsequent degradation and allows mutated α-GalA to reach the lysosomes. However, this drug has an important limitation since DGJ is not effective for all the mutations responsible of Fabry disease, and this statement can be confirmed in the list of mutations that can be treated with DGJ published by European Medicine Agency (technical file of the product for the Galafold of the EMA (Annex I), Spanish version (WC500208434)). The fact that DGJ is not effective for all the mutations responsible for Fabry disease, makes it necessary to look for alternative treatments that can be effective for a wide number of mutations in the GLA gene, which are responsible for Fabry disease, with special emphasis on those mutations, responsible for the disease, for which an effective oral treatment is not available.

There is, therefore, the need to develop new drugs that allow the treatment of lysosomal storage diseases caused by partial or total impairment of the enzymes involved in the metabolism of lysosomal substrates, due to the incorrect folding of these proteins, and with special regard to those diseases that still do not present an adequate and effective treatment, and to those disorders for which there is no available treatment.

In other words, it should be desirable to have effective treatments with a broad spectrum of action increasing the efficacy of the mutated α-GalA enzyme responsible for lysosomal storage diseases.

DESCRIPTION OF THE INVENTION

The object of the present invention is the use of galactose analogues corresponding to the formula (I) which are able to stabilize the structure of the α-galactosidase A (α-GalA) enzyme, by improving its correct folding. At certain concentrations, as discussed herein, the analogues of formula (I) stabilize the structure of α-galactosidase A enzyme, therefore increasing the enzymatic activity of this enzyme.

In a first aspect, the present patent application makes reference to the use of galactose analogues with the following formula:

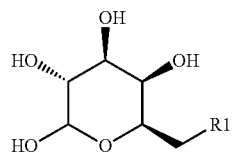

(I)

wherein R1 is selected from the group consisting on an azide ($N_3$), a nitrile (CN), an amine ($NH_2$), an ureide ($NHCONH_2$), a aminomethyl ($NHCH_3$), a methylamine ($CH_2NH_2$), a methylureide ($CH_2NHCONH_2$) and a halogen. Also, the halogen can be I, Br, Cl and F.

In the context of the present invention, these galactose analogues of formula (I) are also called pharmacological chaperones since these molecules have a mechanism of action similar to biological chaperones and are designed to stabilize the structure of certain target proteins. In this protection domain, aforementioned chaperones bind to the target protein, stabilizing its three-dimensional structure, thus allowing said mutated enzyme to acquire its correct folding and be able to perform its biological function.

In the specific case of the present invention, the galactose analogues of formula (I), which are described in the present document, are intended to stabilize the α-galactosidase A.

Pharmacological chaperones described in this document have the ability to increase the enzymatic activity of the α-galactosidase A (α-GalA) enzyme, where the mentioned enzyme present, in turn, at least one of the mutations that affect its folding.

In the context of the present invention, the impairment of the α-GalA enzyme can be caused by at least one mutation, among the more than 600 mutations, that, were described in the GLA gene, and which are responsible of a misfolding of the α-GalA. p.R301Q, p.Q279R, p.P205S, p.L131Q are illustrative examples of the GLA mutations, which allow to demonstrate the efficacy of the galactose analogues of the formula (I), but in no case they represent a limitation, which exclude the efficacy of the galactose analogues, which are object of this invention, on other GLA mutations that cause the decrease or the inactivity of the α-GalA enzyme, due to its misfolding. In the present document, as described below, when the galactose analogues of the formula (I) are administrated in cell cultures with some of the mentioned mutations, a significant increase in the activity of α-GalA can be observed.

Thus, the galactose analogues described in the present document have the ability to bind to the mutated α-GalA enzyme, regardless of whether or not the mutation is in the active site, and stabilize its structure, thereby allowing its correct folding.

It is therefore the object of this invention the medical use of the galactose analogues of the formula (I), and in a preferred embodiment, the use of PB48 and PB51. These compounds can bind to the active site of α-GalA and stabilize its structure to consequently increase its enzymatic activity.

The analogue PB48 presents the following formula:

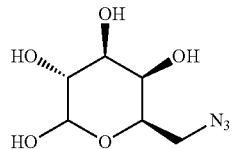 [SMILES: [N-]=[N+]=NC[C@H]1OC(O)[C@H](O)[C@@H](O)[C@H]1O]

The analogue PB51 presents the following formula:

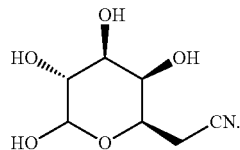 [SMILES: N#CC[C@H]1OC(O)[C@H](O)[C@@H](O)[C@H]1O]

Aforementioned galactose analogues PB48 and PB51 can bind to the active site of the α-GalA by interacting with residues of aspartic acid (D170, D231, D92, D93) and glutamic acid (E203).

It should be noted that the analogues of the formula (I), which are described in the present invention, are generally obtained as a mixture at equilibrium of the alpha and beta isomers. For this reason, analogues compounds of the galactose of the formula (I), preferably PB48 and PB51 or a combination of both, are capable of treating lysosomal storage diseases.

It is, therefore, object of the present invention the use of at least one of the galactose analogues described herein to treat lysosomal storage diseases.

In a preferred embodiment, galactose analogues PB40 and/or PB51 are able to act on the folding of α-GalA to treat Fabry disease.

In a preferred embodiment, it is object of the present invention the use of at least one of the galactose analogues described herein to treat Fabry disease.

Galactose analogues of the formula (I), described in the present document, can be synthesized following and/or adapting procedures described in the following biographical documents:

N. B. Hamadi, M. Msaddek, Synthesis and reactivity of N-sugar-maleimides: an Access to novel highly substituted enantiopure pyrazolines, Tetrahedron: Asymmetry, 2012, 23, 1689-1693.

M. Koketsu, B. Kuberan, R J Linhardt, Stereoselective synthesis of the α-glycoside of a KDO "C"-disaccharide, Organic Letters, 2000, 21, 3361-3363.

J. M. Benito, C. Ortiz Mellet, J. M. Garcia Fernandez, Synthesis of 6,7-dideoxy-7-isothiocyanatoheptoses:

stable fully unprotected monosaccharide isothiocyanates, Carbohydrate Research, 2000, 323, 218-225.

R. W. Binkley, M. G. Ambrose, D. G. Hehemann, Synthesis of Deoxyhalogeno Sugars. Displacement of the (Trifluoromethanesulfonyl)oxy (Triflyl) Group by Halide Ion, Journal of Organic Chemistry, 1980, 45, 4387-4391.

In the present document, a series of tests, where the enzymatic activity of α-GalA is measured to assess the efficiency of the molecules object of the present invention, are described for illustrative purposes. Aforementioned enzymatic activity of α-GalA has been measured in cell lysates by adapting the fluorometric method described by Chamoles et al (Clin Chim Acta 308, 195-196). In synthesis, the assay was performed in 0.15M phosphate-citrate buffer at pH 4.2, using 4-methyllumberiferyl-α-D-galactopyranoside 4 mM (4-MU, #44039, Glycosinth) as substrate and in presence of N-acetyl-D-galactosamine 50 mM. The specific activity of the enzyme is referred to a standard curve of fluorescence/substrate concentration.

It is, also, object of the present invention the pharmacological compositions including an effective amount, ranging, in particular, between 50 mg and 200 mg every 2 days, and in a preferred embodiment, between 145 mg and 155 mg every two days, and in a more preferred embodiment, 150 mg every two days, of the galactose analogues of the formula (I) described in the present document.

Based on the foregoing, the present invention is related to the above pharmacological compositions for the treatment of lysosomal storage diseases.

In addition, in a preferred embodiment, the present invention is also related to the above pharmacological compositions for the treatment of Fabry disease.

In the context of the present invention, effective amount is intended as the minimum amount necessary to observe a therapeutic effect in patients that suffer from a lysosomal storage disease.

In a preferred embodiment of the invention, effective amount is intended as the minimum amount to observe a therapeutic effect in patients suffering Fabry disease.

The galactose analogues of the formula (I), which are described herein, have several advantages over the conventional treatments for the lysosomal storage diseases:

1.—In comparison with ERT therapies, the galactose analogues described herein has a homogeneous distribution since they are small molecules, capable to cross biological membranes, which might include blood-brain barrier. On the contrary, in ERT therapies, recombinant α-GalA is administrated to the patients. The recombinant enzyme enters in the cells transported by the Mannosium-6-phosphate, so, this recombinant enzyme does not reach the tissues that do not express this receptor.

2.—The galactose analogues of the formula (I) have the ability of binding to the mutated α-GalA enzymes, responsible of the Fabry disease which are not possible to treat with the pharmacological chaperones currently in use increasing the therapeutic spectrum of the patients who can use the oral treatment. As an example of the current treatments, the cells presenting the mutation p.Q279R or p.L131Q, to mention a few known mutations, present an increase of the activity of the mutated α-GalA, when they are treated with galactose analogues of the formula (I), whereas the mentioned mutated enzymes do not present the same increase or restoration of activity when they are treated with the approved pharmacological chaperon currently in clinical use.

3.—The cost of production is much lower since the pharmacological chaperones are chemical compounds, their production costs and risk of contamination, with their consequent economic losses, are significantly lower than the production costs of the enzyme replacement therapy, whose drugs are biological.

BRIEF DESCRIPTION OF THE DRAWINGS

FIGS. 1.A and 1.B. Assessment of the increase in the enzymatic activity of α-GalA in a human cell line (293T) transfected with plasmids expressing different mutants of the α-GalA: p.R301Q, p.Q279R, p.P205S, treated with galactose, PB48 and PB51. In the FIG. 1.A, the increase in the enzymatic activity of α-GalA is shown for the three indicated treatments at a concentration of 5 μM. In the case of the FIG. 1.B, the three treatments used are at a concentration of 10 μM. In both figures, 3 columns for each of the mutations are observed. Each one of them represent a treatment to which the human cell line (293T), which was transfected with the plasmids expressing different mutants of the α-GalA, has been subjected. The column on the left (the closest to the vertical coordinate axis), shows cells treated with galactose. The central column represents the cell line treated with PB48. The column on the right (the furthest to the vertical coordinate axis) represents the cell line treated with PB51. The increases in the activity have been calculated by subtracting from each obtained value the value of the activity of α-GalA obtained for the cells, transfected with the corresponding plasmid, which were not treated with any of the tested compounds (untreated cells).

EXAMPLES

Next, we proceed to present, as an explicative example and with no mean to limit the filed of the invention, some results of the efficacy assays, which support the invention, where the enzymatic activity of α-GalA was evaluated, following the treatment with the pharmacological chaperones of the formula (I) described herein.

Experiment 1

PB48 and PB51 analogues were tested at the concentrations of 5 and 10 μM, in a human cell line (293T), transfected with different plasmids expressing different mutants of the α-GalA (p.R301Q, p.Q279R, p.P205S) and their effect were compared with the obtained by treating the same cells with galactose at the same concentration.

As shown in the FIGS. 1.A and 1.B, PB48 and PB51 cause a positive increase in the enzymatic activity of the different α-GalA mutants. The increase of the enzymatic activity of α-GalA is particularly evident in the cells treated with PB48 in most of the cases.

Experiment 2

Figure 2:
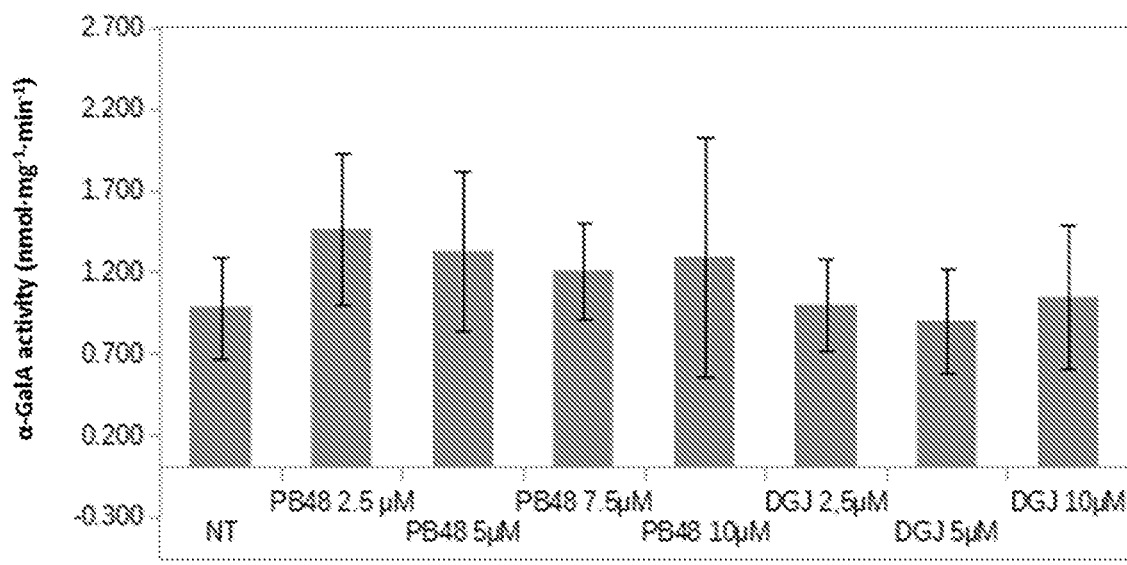
FIG. 2. Assessment of the enzymatic activity of α-GalA in cells (leukocytes) extracted from three hemizygous patients with Fabry disease carrying the mutation p.Q279R on the α-GalA. The mentioned cells were treated with PB48 at concentrations of 2.5 μM, 5 μM, 7.5 μM and 10 μM and with DGJ at concentrations of 2.5 μM, 5 μM and 10 μM.

Similar studies were carried out in leukocytes extracted from peripheral blood of 3 hemizygous patients for the mutation p.Q279R. In these studies, the activity of α-GalA was evaluated in cells treated with PB48 at the concentrations of 2.5 μM, 5 μM, 7.5 μM and 10 μM and with DGJ at the concentrations of 2.5 μM, 5 μM and 10 μM. As shown in FIG. 2, PB48 significantly increases the activity of α-GalA at the concentrations of 2.5 μM, 5 μM and 7.5 μM and is more effective than DGJ in cells of hemizygous patients with the mutation p.Q279R.

Figure 3:
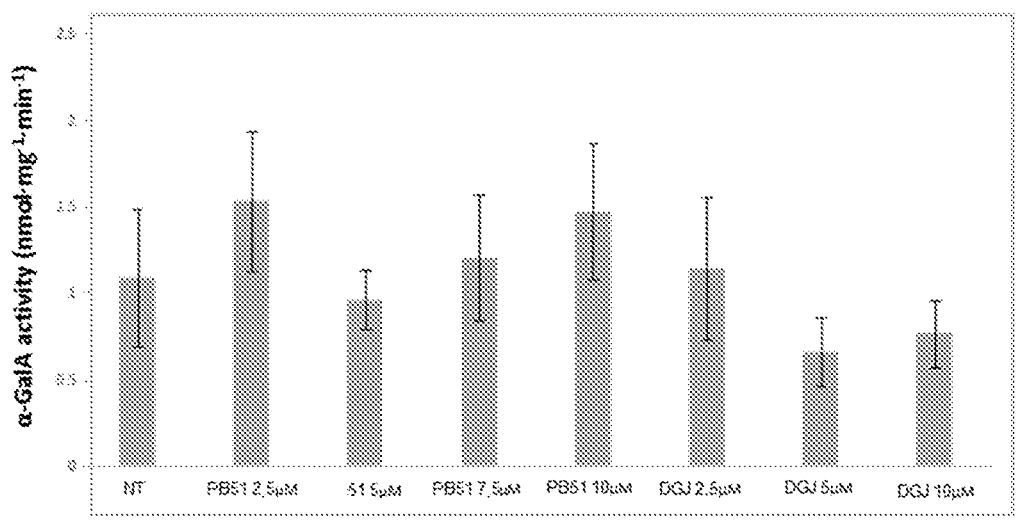
FIG. 3. Assessment of the enzymatic activity of α-GalA in cells (leukocytes) extracted from one hemizygous patient carrying the mutation p.Q279R on the α-GalA. The mentioned cells were treated with PB51 at concentrations of 2.5 μM, 5 μM, 7.5 μM and 10 μM and with DGJ at concentrations of 2.5 μM, 5 μM and 10 μM.

On the other hand, the activity of α-GalA was also tested in cells of a hemyzigous patient with the mutation p.Q279R treated with PB51 at the concentrations of 2.5 μM, 5 μM, 7.5 μM and 10 μM and with DGJ at concentrations of 2.5 μM, 5 μM and 10 μM, see FIG. 3.

As shown in FIG. 3, PB51 determines an increase of the enzymatic activity, which is higher than the one obtained for the treatment with DGJ. The treatment with PB51 at the concentration of 2.5 μM also determines an increase in α-GalA activity in comparison with untreated cells.

Therefore, these results demonstrate that the analogues described in the present document, and in particular PB48, are a very suitable alternative for the patients suffering Fabry disease, and who cannot be treated with DJG, since a treatment based on DGJ do not determines the necessary increase of activity for the treatment of the disease on the mutated α-GalA, when the mutation of the GLA gene is the p.Q279R.

Experiment 3

Studies were carried out on the activity of α-GalA in leukocytes extracted from peripheral blood of a hemizygous patient with the mutation p.Q279R (group of hemizygous cells), a heterozygous patient, and two healthy volunteers (a male and a female, indicated as control). In the presented studies the α-GalA activity was evaluated in cells treated with PB48 at the concentrations of 5 μM, and 10 μM. In a second group cells were treated with PB51 at concentrations of 5 μM, and 10 μM and with DGJ at concentrations of 5 μM, and 10 μM. In order to compare the results obtained for the treatments with the galactose analogues that are described herein, the assessment of α-GalA activity was performed for the same groups of patients' cells, following treatment with galactose at the concentration of 5 μM, and in patients' cells groups, which were not subjected to any treatment.

Figure 4:
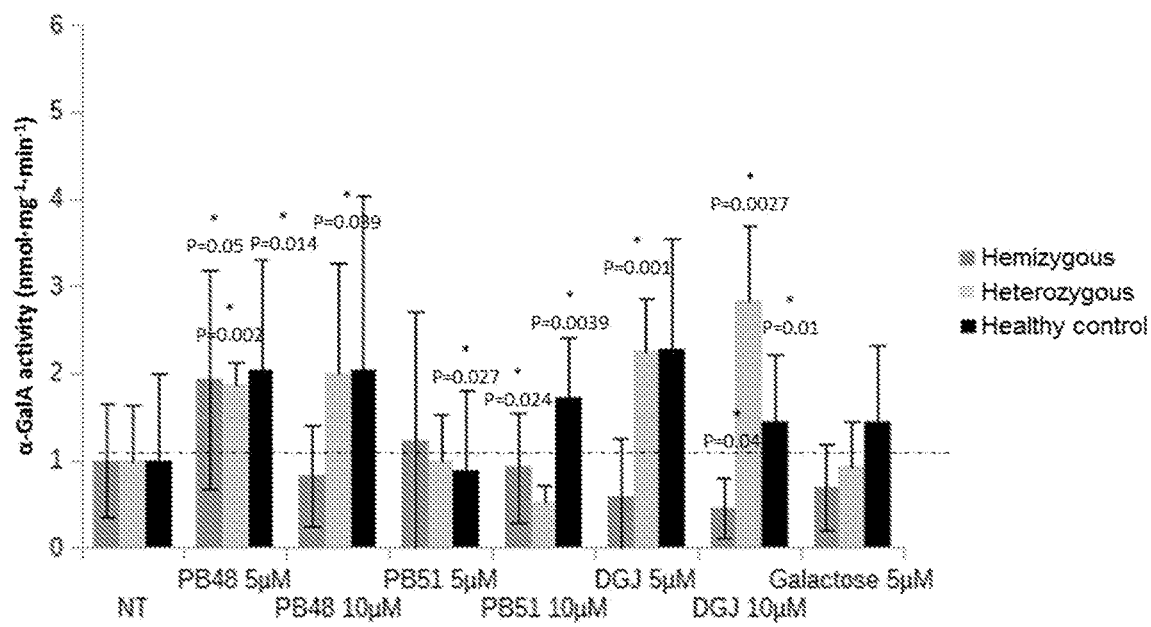
FIG. 4. Assessment of the enzymatic activity of α-GalA in cells extracted from a hemizygous patient expressing the mutation p.Q279R, a heterozygous patient with the mutation p.Q279R and healthy volunteers, treated with PB48 at concentrations of 5 μM and 10 μM, PB51 at concentrations of 5 μM and 10 μM, DGJ at concentrations of 5 μM and 10 μM, and galactose at a concentration of 5 μM. For each one of the treatments 3 columns are shown, representing the cell groups that have been subjected to each one of the treatments. The column on the left (the closest to the vertical coordinate axis), represents leukocytes extracted from peripheral blood of one hemizygous patient for p.Q279R (group of hemizygous cell). The central column represents leukocytes extracted from peripheral blood of one heterozygous patient. The column on the right (the furthest of the vertical coordinate axis) shows leukocytes extracted from peripheral blood extracted of two healthy volunteers, one male and one female (controls). In the vertical axis, the activity of α-GalA, normalized to the untreated control, is represented.

As shown in the FIG. 4, PB48, at the concentration of 5 μM, causes a significant increase of the enzymatic activity in comparison with DGJ, at the same concentration, in the cells of the hemizygous patient and a significant increase of the activity with respect to the untreated cells. The values of the α-GalA activity were normalized to the untreated control, that is, the value of α-GalA enzymatic activity in the samples that have been subjected to each one of the pharmacological treatment (PB48, PB51 or DGJ) was divided by the α-GalA activity value obtained in the corresponding untreated control sample (value of α-GalA activity obtained in the cells of each patients who has not received the treatment).

On the other hand, it has been observed that DGJ (5 μM) is more effective than PB48 (504) as stabilizer of the protein when tested in the leukocytes of the heterozygous patient. This leads to the conclusion that DGJ (504) can be a more efficient chaperone for the α-Gal A native form (wild type), while PB48 at the same concentration is more efficient than DGJ when the mutated form of the enzyme (p.Q279R) is exclusively present.

The data obtained in healthy controls at the same concentration (5 μM) confirm this conclusion.

Experiment 4

PB48 and DGJ were tested in cells (leukocytes) from a hemizygous patient with the p.L131Q mutation of the α-GalA, which produces the classic phenotype of the Fabry disease and a heterozygous patient with the same mutation (p.L131Q), who also expresses the wild type allele of the enzyme.

Figure 5:
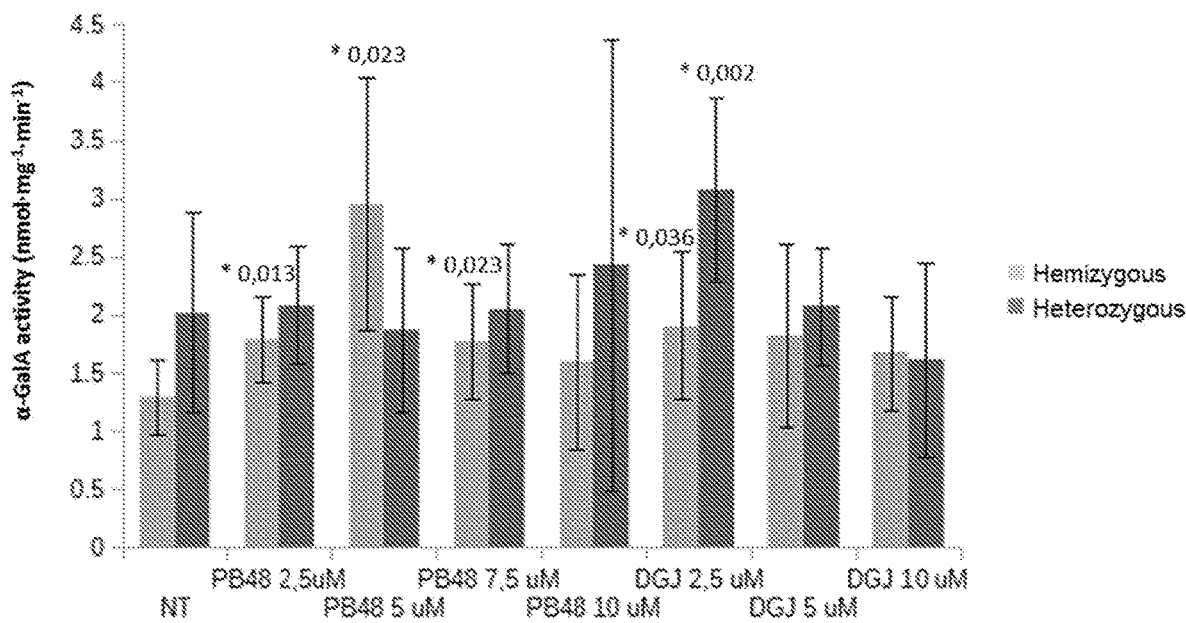
FIG. 5. Assessment of the enzymatic activity of the α-GalA with the mutatation p. L131Q in cells extracted (from a hemizygous patient and a heterozygous patient) treated with PB48 at concentrations of 2.5 μM, 5 μM, 7.5 μM and 10 μM or with DGJ at concentrations of 2.5 μM, 5 μM and 10 μM. For each one of the treatments at the specified concentration, 2 columns are observed, which represent the cell groups that were subjected to those treatments. The column on the left (the closest to the vertical coordinate axis), represents leukocytes extracted from peripheral blood of one hemizygous patient with the p.L131Q mutation. The column on the right (the furthest of the vertical coordinate axis) shows leukocytes extracted from peripheral blood of a heterozygous patient for with the p.L131Q mutation.

As observed in FIG. 5, the enzymatic activity of the α-GalA is significantly higher in cells of the hemizygous patient treated with PB48 at the concentration of 5 μM when compared with untreated cells and with cells treated with DGJ at the same concentration. On the other hand, it can be verified that the enzymatic activity of the α-GalA is higher in the cells of the heterozygous patient treated with DGJ.

The invention claimed is:

1. A method of treating Fabry disease comprising administering a pharmaceutical composition comprising a galactose analogue represented by the following formula:

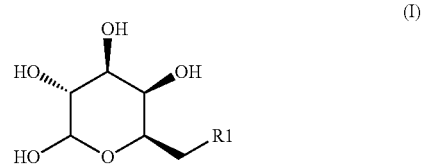

(I)

wherein R1 is selected from the group consisting of N₃ and CN, NH₂, NHCONH₂, NHCH₃, CH₂NH₂ and CH$_2$NHCONH$_2$, and wherein Fabry disease is caused by a mutation affecting the folding of the enzyme α-galactosidase A, wherein the mutation is selected from the group consisting of p.R301Q, p.Q279R, p.P205S and p.L131Q.

2. The method according to claim 1, wherein R1 is selected from the group consisting of N$_3$ and CN.

3. The method according to claim 1, wherein R1 is selected from the group consisting of N$_3$ and CN.

* * * * *